US011304863B2

(12) United States Patent
Hoysan et al.

(10) Patent No.: US 11,304,863 B2
(45) Date of Patent: Apr. 19, 2022

(54) SYSTEM AND METHOD FOR MOUNTING VENTILATOR ON WHEELCHAIR

(71) Applicant: KONINKLIJKE PHILIPS N.V., Eindhoven (NL)

(72) Inventors: David Hoysan, Pittsburgh, PA (US); Matthew Answine, Apollo, PA (US)

(73) Assignee: Koninklijke Philips N.V., Eindhoven (NL)

( * ) Notice: Subject to any disclaimer, the term of this patent is extended or adjusted under 35 U.S.C. 154(b) by 735 days.

(21) Appl. No.: 16/103,146

(22) Filed: Aug. 14, 2018

(65) Prior Publication Data

US 2019/0053963 A1 Feb. 21, 2019

Related U.S. Application Data

(60) Provisional application No. 62/545,496, filed on Aug. 15, 2017.

(51) Int. Cl.
*A61G 5/10* (2006.01)
*A61M 16/10* (2006.01)
*A61M 16/00* (2006.01)

(52) U.S. Cl.
CPC ............. *A61G 5/10* (2013.01); *A61M 16/022* (2017.08); *A61M 16/10* (2013.01); *A61G 2203/70* (2013.01); *A61M 16/0003* (2014.02); *A61M 2202/0208* (2013.01); *A61M 2205/42* (2013.01); *A61M 2205/8206* (2013.01); *A61M 2209/082* (2013.01); *A61M 2209/084* (2013.01)

(58) Field of Classification Search
CPC ... A61G 5/10; A61G 2203/70; A61M 16/022; A61M 16/10; A61M 16/003; A61M 2202/0208; A61M 2205/042; A61M 2209/082; A61M 2209/084
See application file for complete search history.

(56) References Cited

U.S. PATENT DOCUMENTS

| 6,216,927 | B1 | | 4/2001 | Meritt | |
|---|---|---|---|---|---|
| 6,273,444 | B1 | * | 8/2001 | Power | A61G 5/10 280/204 |
| 6,481,739 | B1 | * | 11/2002 | Newkirk | A61G 7/05 267/69 |
| 7,334,712 | B2 | * | 2/2008 | Hassett | A44B 19/262 224/268 |
| 8,763,971 | B1 | * | 7/2014 | Wilson | A61M 16/021 248/340 |
| 2005/0105254 | A1 | | 5/2005 | Lee | |

(Continued)

FOREIGN PATENT DOCUMENTS

EP 2671607 A1 12/2013
TW M509031 U 9/2015

*Primary Examiner* — Minnah L Seoh
*Assistant Examiner* — Harold Eric Pahlck, III
(74) *Attorney, Agent, or Firm* — Daniel H. Brean

(57) ABSTRACT

A system for mounting a ventilator on a wheelchair is provided. The system comprises a first member and a second member. The first member is configured to be releasably fastened to the wheelchair. The first member comprises a first coupler structure. The second member is coupled with the ventilator. The second member comprises a second coupler structure that is configured to be releasably coupled with the first coupler structure to mount the ventilator on the wheelchair.

10 Claims, 13 Drawing Sheets

(56) References Cited

U.S. PATENT DOCUMENTS

2008/0067207 A1\* 3/2008 Behrhorst ............ A61G 5/1054
224/407
2009/0020575 A1 1/2009 Katchen
2018/0325757 A1\* 11/2018 Schmid ................ A61G 5/1094

\* cited by examiner

Prior Art

SYSTEM AND METHOD FOR MOUNTING VENTILATOR ON WHEELCHAIR

CROSS-REFERENCE TO RELATED APPLICATIONS

This patent application claims the priority benefit under 35 U.S.C. § 119(e) of U.S. Provisional Application No. 62/545,496, filed on Aug. 15, 2017, the contents of which are herein incorporated by reference.

BACKGROUND OF THE INVENTION

1. Field of the Invention

The present patent application pertains to a system and a method for mounting a ventilator on a wheelchair.

2. Description of the Related Art

Homecare ventilators are frequently mounted onto the back of wheelchairs to enable therapy while on the go. Different ventilators have different mounting solutions, each having different challenges when trying to mount to a wide variety of wheelchairs. The wide variety of wheelchair configurations makes it difficult to provide a standard way of mounting ventilators to the back of wheelchairs.

FIGS. 1-3 show three different prior art mount solutions to mount the same ventilator V on different wheelchairs $W_1$, $W_2$ and $W_3$. For example, FIG. 1 shows ventilator V disposed in a soft bag B. Soft bag B has riveted holes secured to a mechanical mount harness H that is coupled to wheelchair $W_1$. FIG. 2 shows a hard shell ventilator support $HS_1$ that is mechanically fastened to a channel C on the back of wheelchair $W_2$. FIG. 3 shows a hard shell ventilator support $HS_2$ strapped to the back of wheelchair $W_3$. The different wheelchair geometry requires different third party mount solutions or people to create their own innovative ways to mount ventilator V on wheelchair $W_1$, $W_2$ or $W_3$.

SUMMARY

Accordingly, it is an object of one or more embodiments of the present patent application to provide a system for mounting a ventilator on a wheelchair. The system comprises a first member, and a second member. The first member is configured to be releasably fastened to the wheelchair. The first member comprises a first coupler structure. The second member is coupled with the ventilator. The second member comprises a second coupler structure that is configured to be releasably coupled with the first coupler structure to mount the ventilator on the wheelchair.

It is yet another aspect of one or more embodiments of the present patent application to provide a method for mounting a ventilator on a wheelchair. The method comprises releasably fastening a first member to the wheelchair, the first member comprising a first coupler structure; coupling a second member with the ventilator, the second member comprises a second coupler structure; and releasably coupling the second coupler structure with the first coupler structure to mount the ventilator on the wheelchair.

It is yet another aspect of one or more embodiments of the present patent application to provide a system for mounting a ventilator on a wheelchair. The system comprises means for releasably fastening to the wheelchair, the means for releasably fastening comprising a first means for releasably coupling; and means for coupling with the ventilator, the means for coupling comprising a second means for releasably coupling that is configured to be releasably coupled with the first means for releasably coupling to mount the ventilator on the wheelchair.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
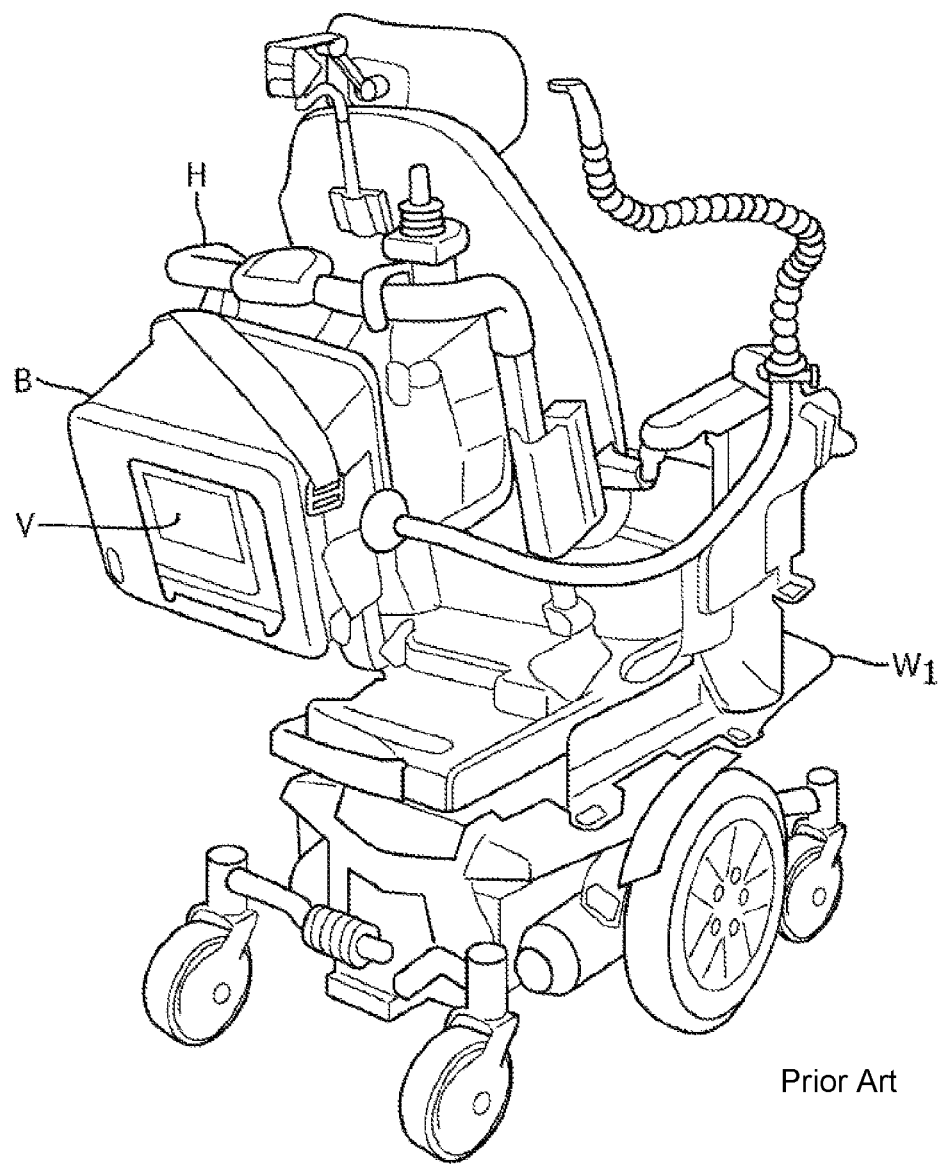
FIG. 1 shows a prior art system for mounting a ventilator on a wheelchair.
Figure 2:
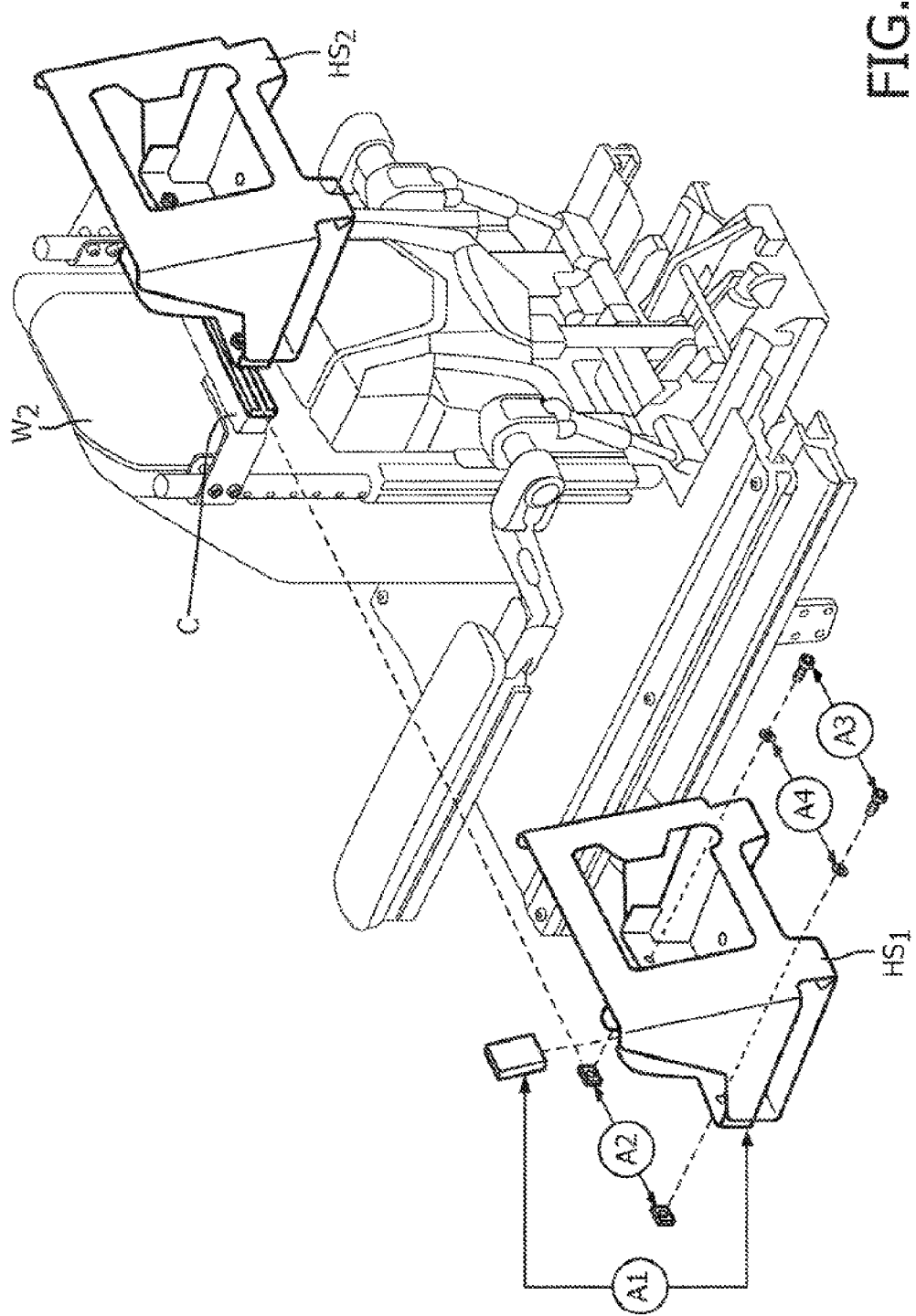
FIG. 2 shows another prior art system for mounting the same ventilator of FIG. 1 on a different wheelchair.
Figure 3:
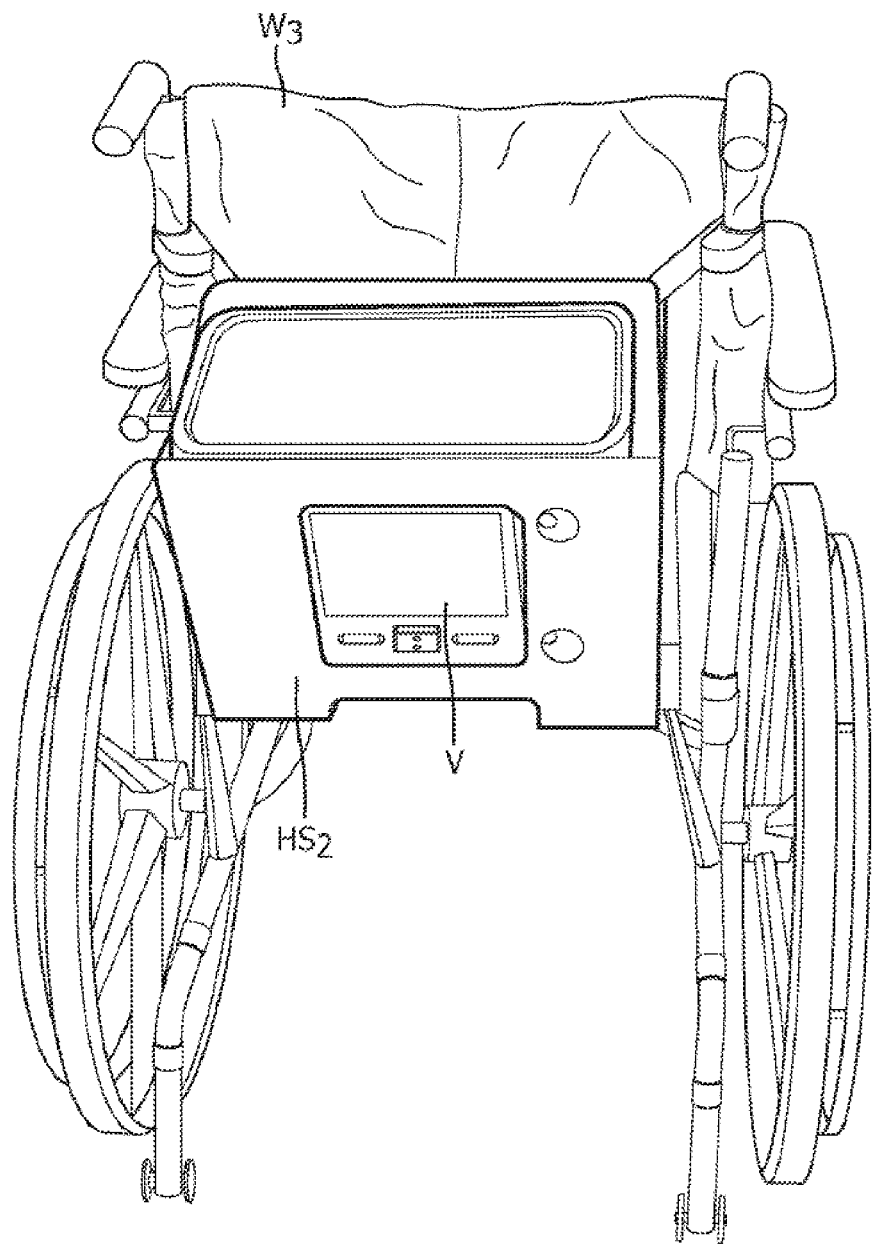
FIG. 3 shows yet another prior art solution for mounting the same ventilator of FIG. 1 on a different wheelchair.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

In one embodiment, referring to FIGS. 4-7, a system 100 for mounting a ventilator 102 on a wheelchair 104 is provided. System 100 comprises a first member 106 and a second member 108. First member 106 is configured to be releasably fastened to wheel chair 104. First member 106 comprises a first coupler structure 110. Second member 108 is coupled with the ventilator 102. Second member 108 comprises a second coupler structure 112 that is configured to be releasably coupled with first coupler structure 110 to mount ventilator 102 on wheelchair 104.

Figure 4:
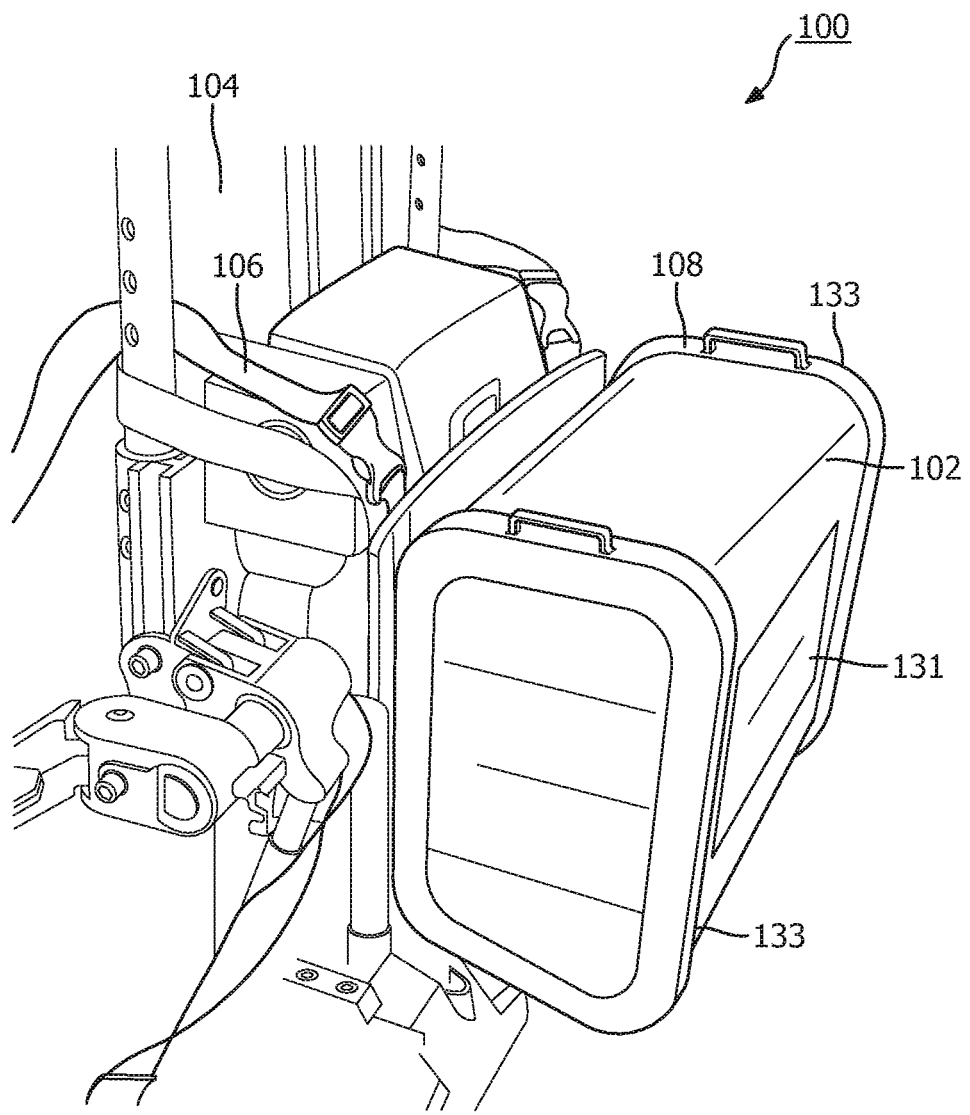
FIG. 4 shows a side perspective view of a system for mounting a ventilator on a wheelchair in accordance with an embodiment of the present patent application.
Figure 5:
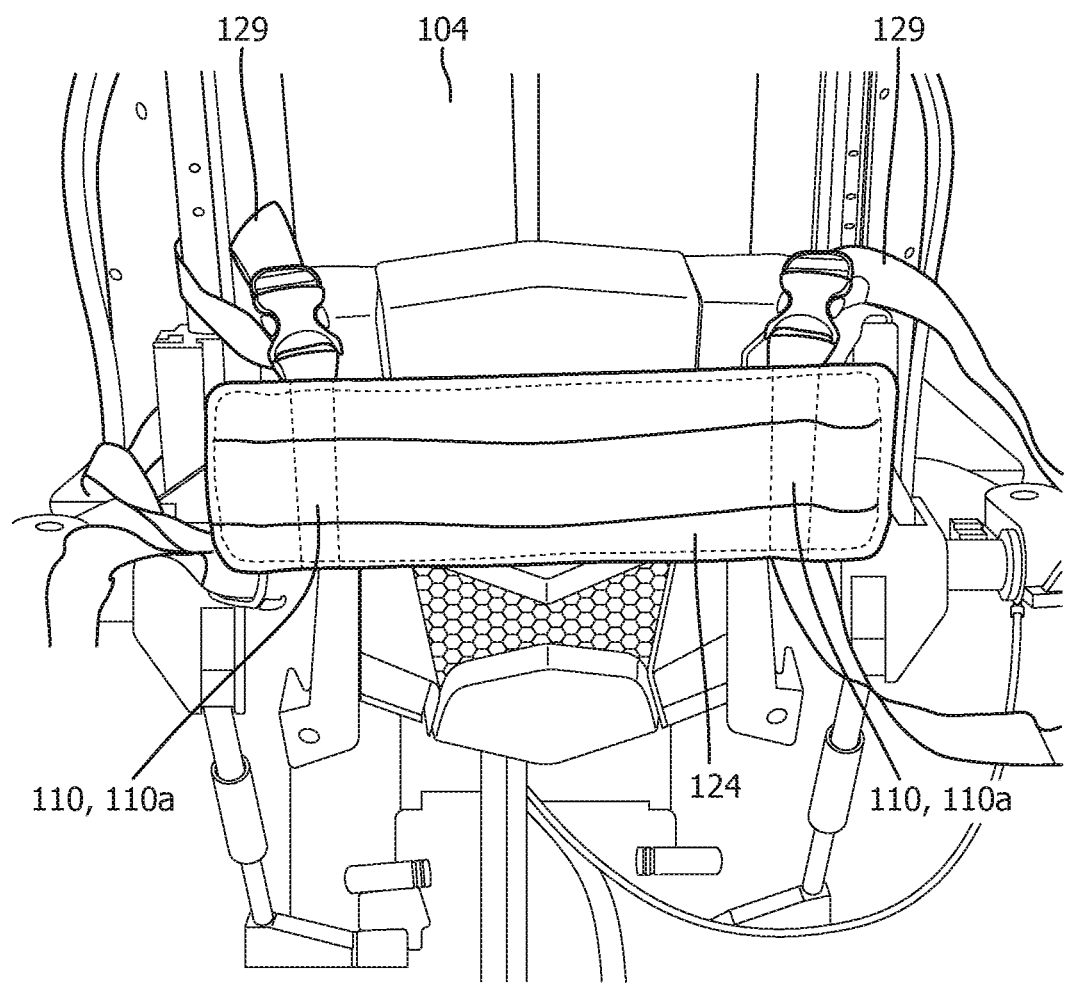
FIG. 5 shows a front perspective view of the system of FIG. 4, where some portions of the system are not shown for sake of clarity and to better illustrate other components of the system.
Figure 6:
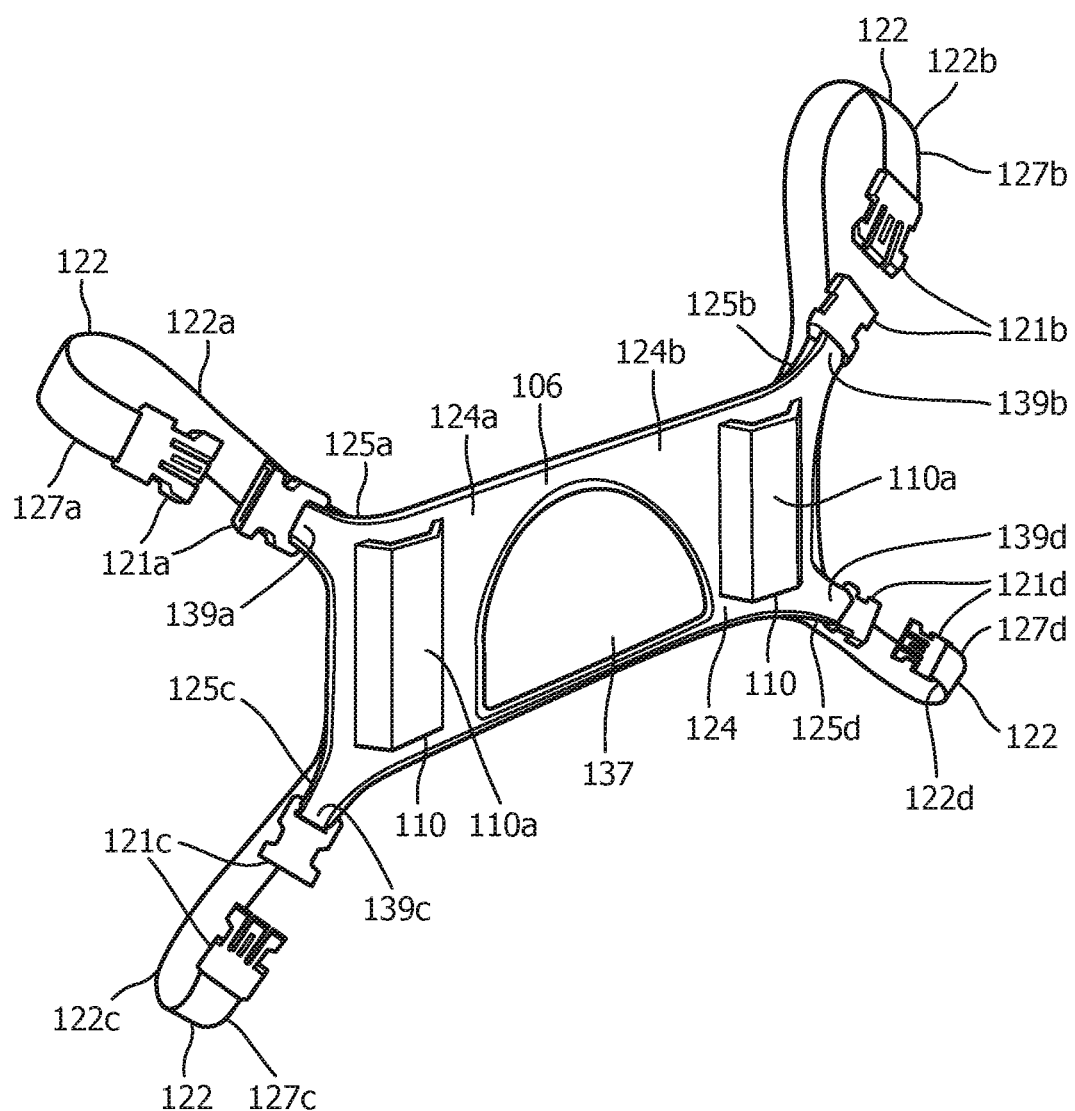
FIG. 6 shows a side perspective view of a first member of the system in accordance with an embodiment of the present patent application.
Figure 7:
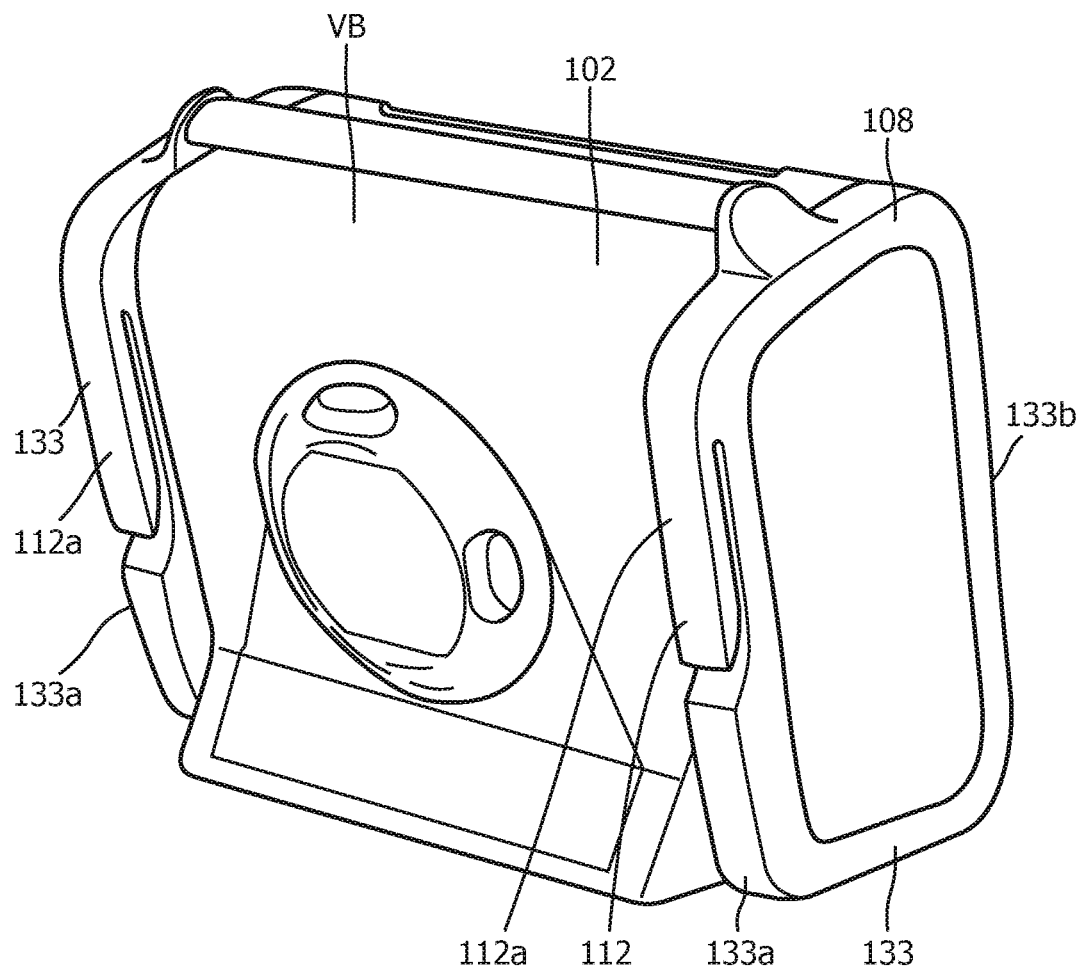
FIG. 7 shows a side perspective view of a second member of the system in accordance with an embodiment of the present patent application.

In one embodiment, system 100 includes a combination of mounting strap as shown in FIG. 6 and mounting elements (e.g., hooks) as shown in FIG. 7. In one embodiment, mounting elements may be part of a ventilator in-use bag/case as shown in FIG. 7. In one embodiment, mounting strap may be adjusted appropriately to attach to the back of wheelchair 104 as shown in FIG. 5. In one embodiment, mounting elements are configured to enable ventilator 102 to be secured on mounting strap as shown in FIG. 4. In one embodiment, mounting elements may also be referred to as second coupler structure 112 of second member 108 and mounting strap may also be referred to as first member 106.

In one embodiment, ventilator 102 is a medical ventilator system or a pressure support device that is configured to deliver a fluid, such as oxygen, air or other oxygen or breathing gas mixture, to an airway of patient to augment or substitute the patient's own ventilatory effort. For example, in one embodiment, ventilator 102 generally includes a primary gas flow delivery system, which includes a pressure/flow generator, a pressure/flow control element, and a flow sensor. The generator receives a flow of breathing gas, such as air, oxygen, or an oxygen mixture through an optional noise suppression device from a supply of breathing gas. The generator elevates the pressure of the received breathing gas to generate a flow of breathing gas for delivery to an airway of a patient.

In one embodiment, ventilator 102 includes the supply of breathing gas or an oxygen source. In one embodiment, ventilator 102 includes an internal rechargeable battery pack that is disposed within an interior of a ventilator housing and/or a detachable battery pack that is removably coupled to the exterior of the ventilator housing.

In one embodiment, system 100 is configured to mount other medical device (e.g., other than ventilator 102 or the pressure support device described above) on wheelchair 104. For example, the other medical device may include a medical device used in secretion management, a medical device used in sleep therapy (e.g., PAPs, BiPAPs, etc.), a cardiac pacing device, a medical therapeutics device, a medical monitoring device, and/or other portable medical devices.

In one embodiment, wheelchair 104 may be any two-wheeled wheelchair, any three-wheeled wheelchair, any four-wheeled wheelchair or any five-wheeled wheelchair. In one embodiment, wheelchair 104 may be a motorized or electrically powered wheelchair or a manual propulsion wheelchair. In one embodiment, wheelchair 104 may be a mobility scooter. In one embodiment, wheelchair 104 may generally include a frame, a set of wheels/rollers rotatably attached to the frame, a seat and a backrest both disposed on the frame, and optional foot rests. The set of wheels/rollers may include caster wheels at the front of the frame and two large wheels at the back of the wheelchair frame.

Figure 11:
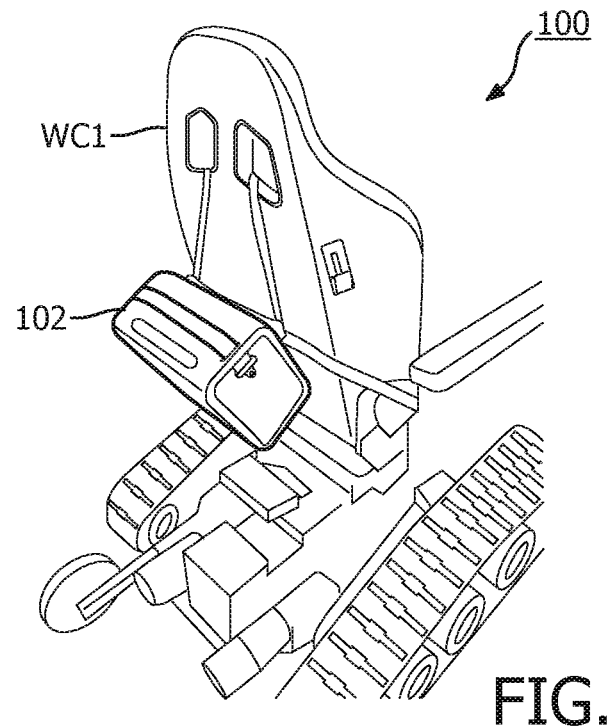
FIGS. 11-16 show a system in accordance with an embodiment of the present patent application being used for mounting the same ventilator on several different types of wheelchairs.
Figure 12:
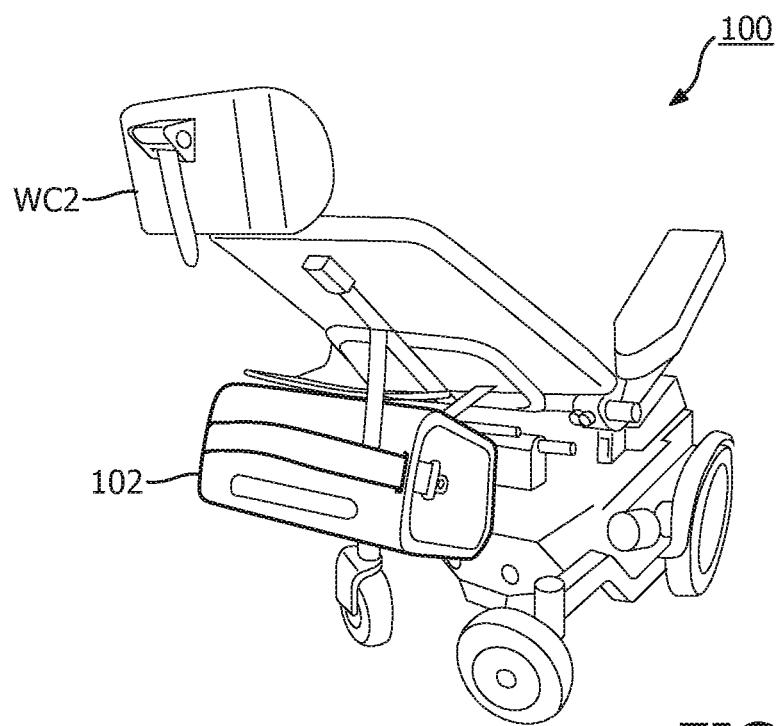
Figure 13:
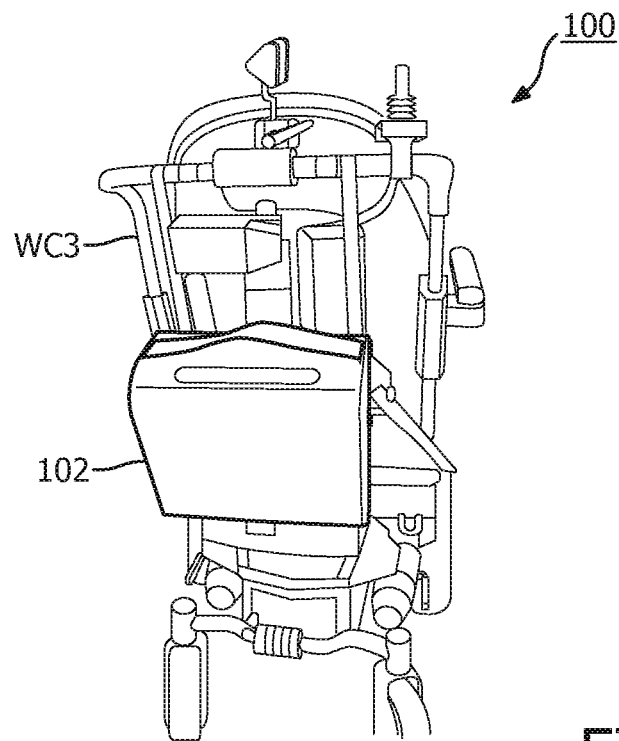
Figure 14:
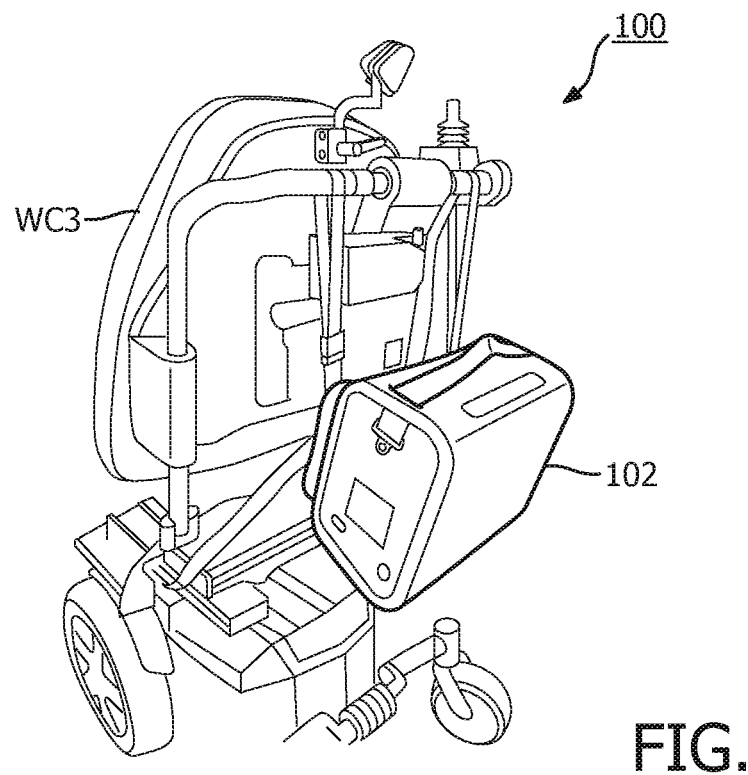
Figure 15:
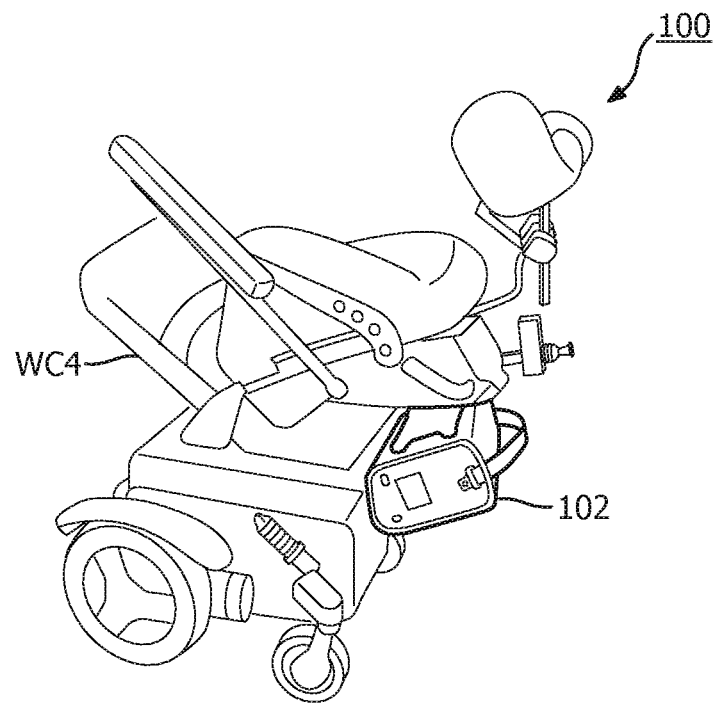
Figure 16:
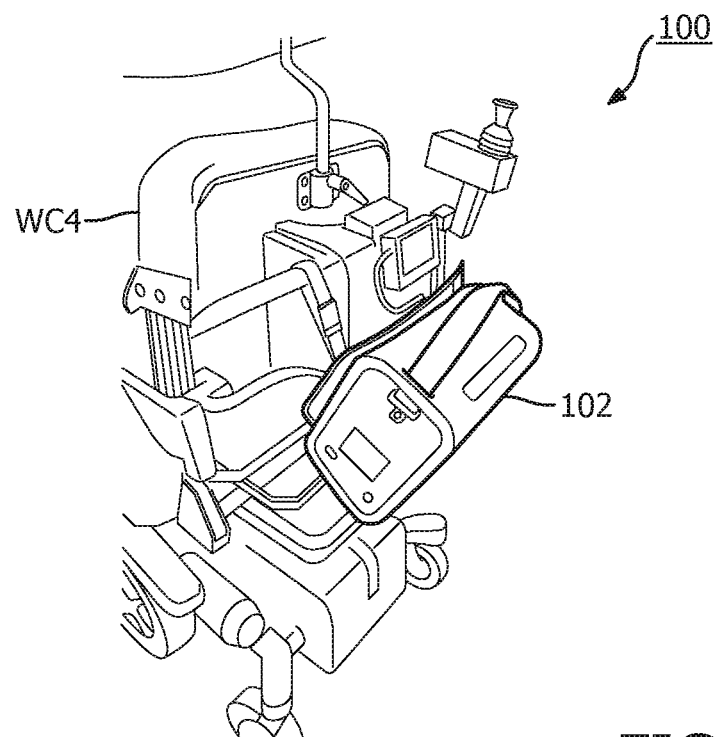

In one embodiment, system 100 is configured to mount ventilator 102 on any one of several different types of wheelchairs. For example, in one embodiment, system 100 is used to mount same ventilator 102 on wheelchair $WC_1$ as shown in FIG. 11, wheelchair $WC_2$ as shown in FIG. 12, wheelchair $WC_3$ as shown in FIGS. 13 and 14, and wheelchair $WC_4$ as shown in FIGS. 15 and 16.

In one embodiment, first member 106, as shown in FIGS. 5 and 6, includes a first support member 124 and webbing 122. In one embodiment, first support member 124 has generally rectangular shaped configuration. In one embodiment, the length of first support member 124 is 12 inches. In one embodiment, the length of first support member 124 is in the range between 4 and 24 inches. In one embodiment, the height of first support member 124 is 3.5 inches. In one embodiment, the height of first support member 124 is in the range between 1 and 24 inches.

In one embodiment, first support member 124 includes a first support surface 124a and a second support surface 124b. In one embodiment, as shown in FIG. 6, first support member 124 includes an opening 137 that is configured to receive a portion of ventilator 102 therein. In another embodiment, as shown in FIG. 5, opening 137 is optional.

In one embodiment, first support member 124 may be made of a plastic material. In one embodiment, first support member 124 is made of any flexible material. The present patent application also contemplates that first support member 124 may be formed from other materials as would be appreciated by one skilled in the art. In one embodiment, member 124 may be constructed of nylon, plastic, polyester, fabric, or any other flexible or non-flexible material. The present patent application also contemplates that first member 106 and first support member 124 may have other shapes or configurations as would be appreciated by one skilled in the art. For example, first support member 124 has different sizes, shapes and/or configurations in FIGS. 5 and 6.

In one embodiment, first member 106 also includes two or more sets of interengaging fastener elements (e.g., buckle clips/side release clips) 121 a, 121 b, 121 c, and 121 d that are configured to quickly attach first member 106 to wheelchair 104 and to quickly release/detach first member 106 from wheelchair 104. In one embodiment, each of the fastener elements 121 a, 121 b, 121 c, and 121 d includes a female portion and a male portion. In one embodiment, a female portion of each of the fastener elements 121 a, 121 b, 121 c, and 121 d is attached to first support member 124 and a male portion of each of the fastener elements 121 a, 121 b, 121 c, and 121 d is attached to a corresponding strap portion 122, 122 a, 122 b, 122 c, and 122 d, and vice versa.

In one embodiment, instead of the side release clips, first member 106 may include other types of interengaging fastener elements that are configured to quickly attach first member 106 to wheelchair 104 and to quickly release/detach first member 106 from wheelchair 104. For example, these other types of interengaging fastener elements include hook and loop fasteners, such as VELCRO®, snaps, clasps, buttons, clips, buckles, catches, eyelets, etc.

Figure 8:
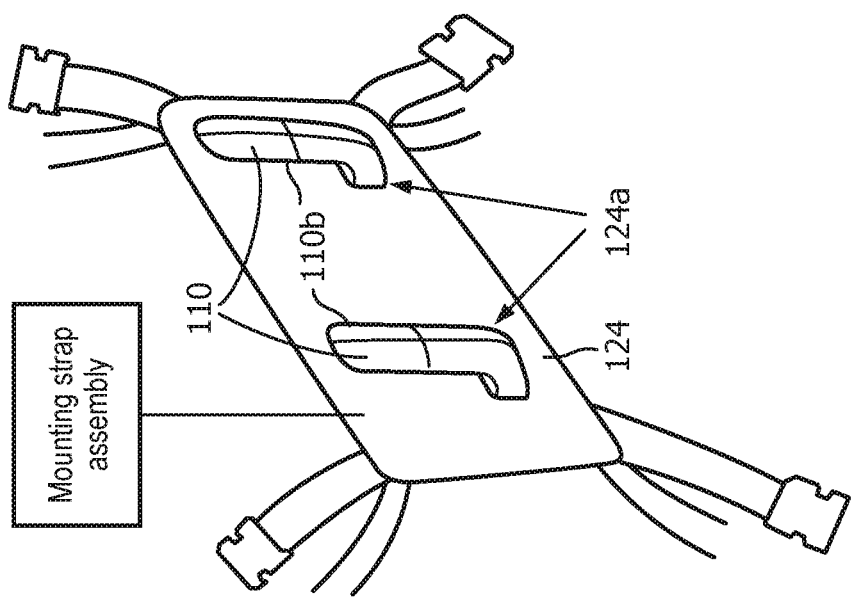
FIG. 8 shows a side perspective view of a first member of a system in accordance with another embodiment of the present patent application.

In one embodiment, as shown in FIGS. 6 and 8, female portions (or male portions) of each of the fastener elements 121a, 121b, 121c, and 121d that are attached to first support member 124 at its end portions 139a, 139b, 139c, and 139d. In another embodiment, as shown in FIG. 5, female portions (or male portions) of each of the fastener elements 121a, 121b, 121c, and 121d may be attached to first support member 124 anywhere along its length dimension as long as first member 106 can be releasably fastened to wheelchair 104.

In one embodiment, webbing 122 may be made of a fabric, a nylon, a polyester, a plastic, or other lightweight and non-elastic material. The present patent application also contemplates that webbing 122 may be formed from other materials as would be appreciated by one skilled in the art. In one embodiment, member 122 could be made of rubber in addition to the materials noted. In one embodiment, webbing 122 includes one or more strap portions or members. In the illustrated embodiment, webbing 122 includes four strap portions or members 122, 122a, 122b, 122c, and 122d.

In one embodiment, the length of each strap portions or members 122a, 122b, 122c, and 122d is 24 inches. In one embodiment, the length of each strap portions or members 122a, 122b, 122c, and 122d is in the range between 4 and 60 inches. In one embodiment, the width of each strap portions or members 122a, 122b, 122c, and 122d is 1 inch. In one embodiment, the width of each strap portions or members 122a, 122b, 122c, and 122d is in the range between 0.5 and 4 inches.

In one embodiment, ends 125a, 125b, 125c, 125d of strap portions or members 122a, 122b, 122c, and 122d are fastened to rear/second support surface 124b of first support member 124 and free ends 127a, 127b, 127c, 127d of strap portions or members 122a, 122b, 122c, and 122d are attached to corresponding one (e.g., male or female portion) of the fastener elements 121a, 121b, 121c, and 121d.

In one embodiment, free ends 127a, 127b, 127c, 127d of strap portions or members 122a, 122b, 122c, and 122d are configured to be looped around a portion 129 of wheel chair 104. In one embodiment, portion 129 of wheelchair 104 may be a backrest, back support member, side support member or any other member or support member of wheelchair 104. In one embodiment, strap portions or members 122a, 122b, 122c, and 122d are then tightly secured around portion 129 of wheelchair 104 by their corresponding fastener elements 121a, 121b, 121c, and 121d. In one embodiment, each of strap portions or members 122a, 122b, 122c, and 122d may be individually adjustable in length so that first member 106 may be adjusted for wheelchairs having different sizes, shapes and configurations. In one embodiment, each of strap portions or members 122a, 122b, 122c, and 122d may be easily adjusted as needed by user. In one embodiment, first member 106 may be permanently attached to the back of wheelchair 104.

In one embodiment, first coupler structure 110 is disposed on first/front support surface 124a of first support member 124 of first member 106. In one embodiment, first coupler structure 110 may be in the form of loops 110a as shown in FIG. 6. In another embodiment, first coupler structure 110 may be in the form of hooks 110b as shown in FIG. 8. In one embodiment, first member 106 and second member 108, as shown in and described with respect to FIGS. 8-10, have the same structure, configuration and operation as that of first member 106 and second member 108, as shown in and described with respect to FIGS. 4-7, except for the differences discussed here.

In one embodiment, second member 108, as shown in FIGS. 4 and 7, is made of a plastic material. The present patent application also contemplates that second member 108 may be formed from other materials as would be appreciated by one skilled in the art. In one embodiment, member 108 may also be constructed of rubber or metal.

In one embodiment, second member 108 may be removably attached to a ventilator in-use bag or case VB. In one embodiment, second member 108 may be permanently attached to ventilator in-use bag/case VB. In one embodiment, second member 108 may be molded into a ventilator in-use bag/case VB.

In one embodiment, ventilator in-use bag/case VB is configured to protect ventilator 102 during its transportation, storage and use. In one embodiment, ventilator in-use bag/case VB is compact and easy to use. In one embodiment, ventilator in-use bag/case VB includes a frame and a cover formed over the frame. The frame may include walls to define a compartment for receiving ventilator 102. In one embodiment, ventilator in-use bag/case VB may also include cushioning materials that is configured to protect ventilator 102 during its transportation, storage and use. In one embodiment, as shown in FIG. 4, ventilator in-use bag/case VB is configured such that the operational control panels 131 of ventilator 102 are accessible without removing the ventilator 102 from ventilator in-use bag/case VB. In one embodiment, ventilator in-use bag/case VB may have a strap or a handle to facilitate transportation of ventilator 102 and ventilator in-use bag/case g VB. In one embodiment, ventilator in-use bag/case VB may have a soft or a hard shell configuration.

In one embodiment, second member 108 may include one or more second support members 133. In the illustrated embodiment of FIGS. 4 and 7, second member 108 may include two second support members 133 disposed on either sides/ends of ventilator 102 that is received in ventilator in-use bag/case VB. In one embodiment, two second support members 133 of second member 108 may be interconnected to each other. In one embodiment, two second support members 133 of second member 108 may be separate from each other.

In one embodiment, second member 108 and/or one or more second support members 133 may have an annular shaped configuration. The present patent application also contemplates that second member 108 and/or one or more second support members 133 may have other shapes or configurations as would be appreciated by one skilled in the art.

In one embodiment, each second support member 133 includes a front/first support surface 133a and a rear/second support surface 133b. In one embodiment, second coupler structure 112 may be disposed on first/front support surface 133a. In one embodiment, second coupler structure 112 may be in the form of hooks 112a as shown in FIG. 7. In another embodiment, second coupler structure 112 may be in the form of loops 112b as shown in FIG. 9.

In one embodiment, ventilator 102 in ventilator in-use bag/case VB along with second member 108 may be easily attached to or easily detached from first member 106 as needed by the user.

In one embodiment, referring to FIGS. 4-7, loops 110a of first member 106 are configured to be releasable coupled with corresponding hooks 112a disposed on second member 108 to mount ventilator 102 on wheelchair 104. In one embodiment, referring to FIGS. 8-10, hooks 110b of first member 106 are configured to be releasable coupled with corresponding loops 112b disposed on second member 108 to mount ventilator 102 on wheelchair 104.

Figure 9:
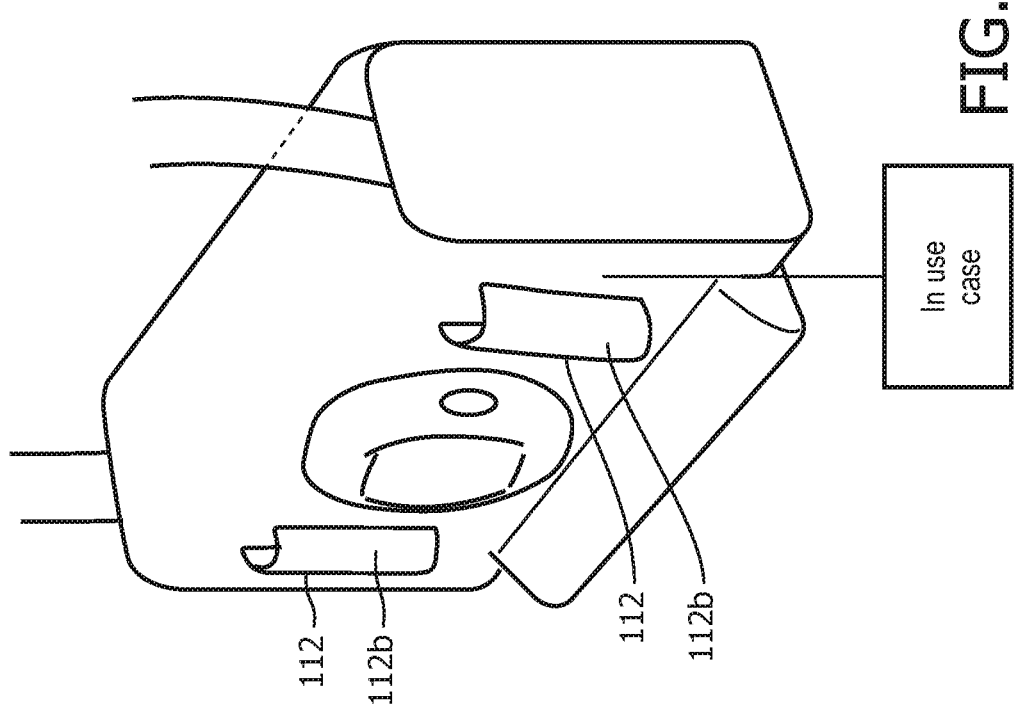
FIG. 9 shows a side perspective view of a second member of a system in accordance with another embodiment of the present patent application.
Figure 10:
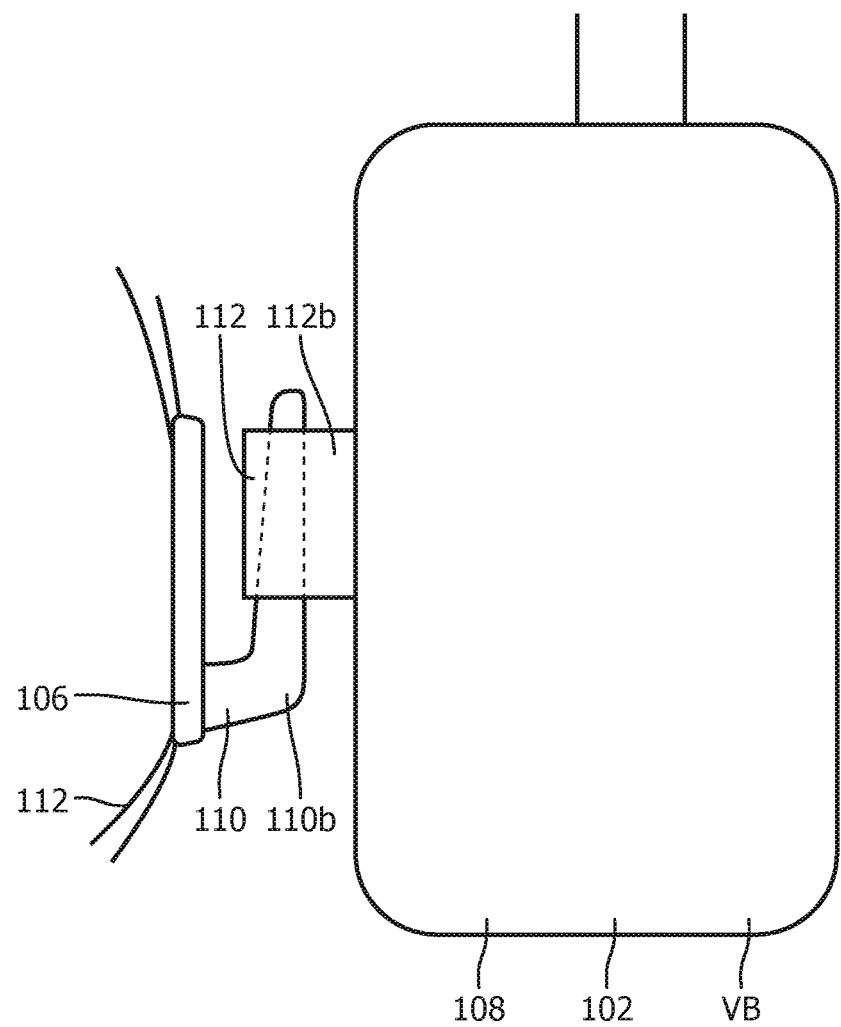
FIG. 10 shows a side view of a system for mounting a ventilator on a wheelchair in accordance with another embodiment of the present patent application, where some portions of the system are not shown for sake of clarity and to better illustrate other components of the system.

In one embodiment, first coupler structure 110, 110a as shown in FIGS. 4-7 and first coupler structure 110, 110b as shown in FIGS. 8-10 are just two examples of first coupler structure 110 of system 100. In one embodiment, first coupler structure 110 may include any fastener for releasably coupling with second coupler structure 110 so as to mount ventilator 102 on wheelchair 104. Similarly, second coupler structure 112, 112a as shown in FIGS. 4-7 and second coupler structure 112, 112b as shown in FIGS. 8-10 are just two examples of second coupler structure 112 of system 100. In one embodiment, second coupler structure 112 may include any fastener for releasably coupling with first coupler structure 110 so as to mount ventilator 102 on wheelchair 104. For example, in one embodiment, first coupler structure 110 and/or second coupler structure 112 may include hook and loop fastener, such as VELCRO®, snaps, magnets, dovetails, clasps, buttons, clips, buckles, catches, eyelets, etc.

In one embodiment, first coupler structure 110 may include a single (rather than two illustrated in FIGS. 4-7 and 8-10) first coupler structure that is disposed centrally on first support structure 124 of first member 106 and that is configured to be releasably coupled with a corresponding single second coupler structure 112 that is centrally disposed on second member 108/ventilator in-use bag/case VB. In one embodiment, the single first and second coupler structures may have a greater width to balance the weight of ventilator 102 on wheelchair 104.

In one embodiment, system 100 may also be used by the patients/users in their home environments or assisted living/residential care facilities. For example, in such an embodiment, system 100 is configured to enable ventilator 102 or any other portable medical device to be mounted on any one of the several different types of patient support structures, including but not limited to, patient beds, chairs, or other patient support structures. For example, in one embodiment, system 100 is also configured to mount a portable medical device on side of the bed or a bed rail of the patient/user's bed in their home or assisted living/residential care facility. In one embodiment, system 100 is configured to enable ventilator 102 or any other medical device to be mounted on any one of several different types of car seats and/or seats in patient transit/transport vehicle. In one embodiment, the other medical device may include a medical device used in secretion management, a medical device used in sleep therapy (e.g., PAPs, BiPAPs, etc.), a cardiac pacing device, a medical therapeutics device, a medical monitoring device, and/or other portable medical devices.

The universal ventilator mounting solution of the present patent application allows ventilator 102 to be mounted to the back of any wheelchair. That is, system 100 provides a "one-size fits all configuration" that is configured to work with any wheelchair.

In one embodiment, the dimensions as described in the present patent application, are up to 5 percent greater than or up to 5 percent less than those described above. In one embodiment, the dimensions as described in the present patent application, are up to 10 percent greater than or up to 10 percent less than those described above. In one embodiment, dimensions as described in the present patent application, are up to 20 percent greater than or up to 20 percent less than those described above. In one embodiment, all the dimensions as described in the present patent application are in inches.

Figure 17:
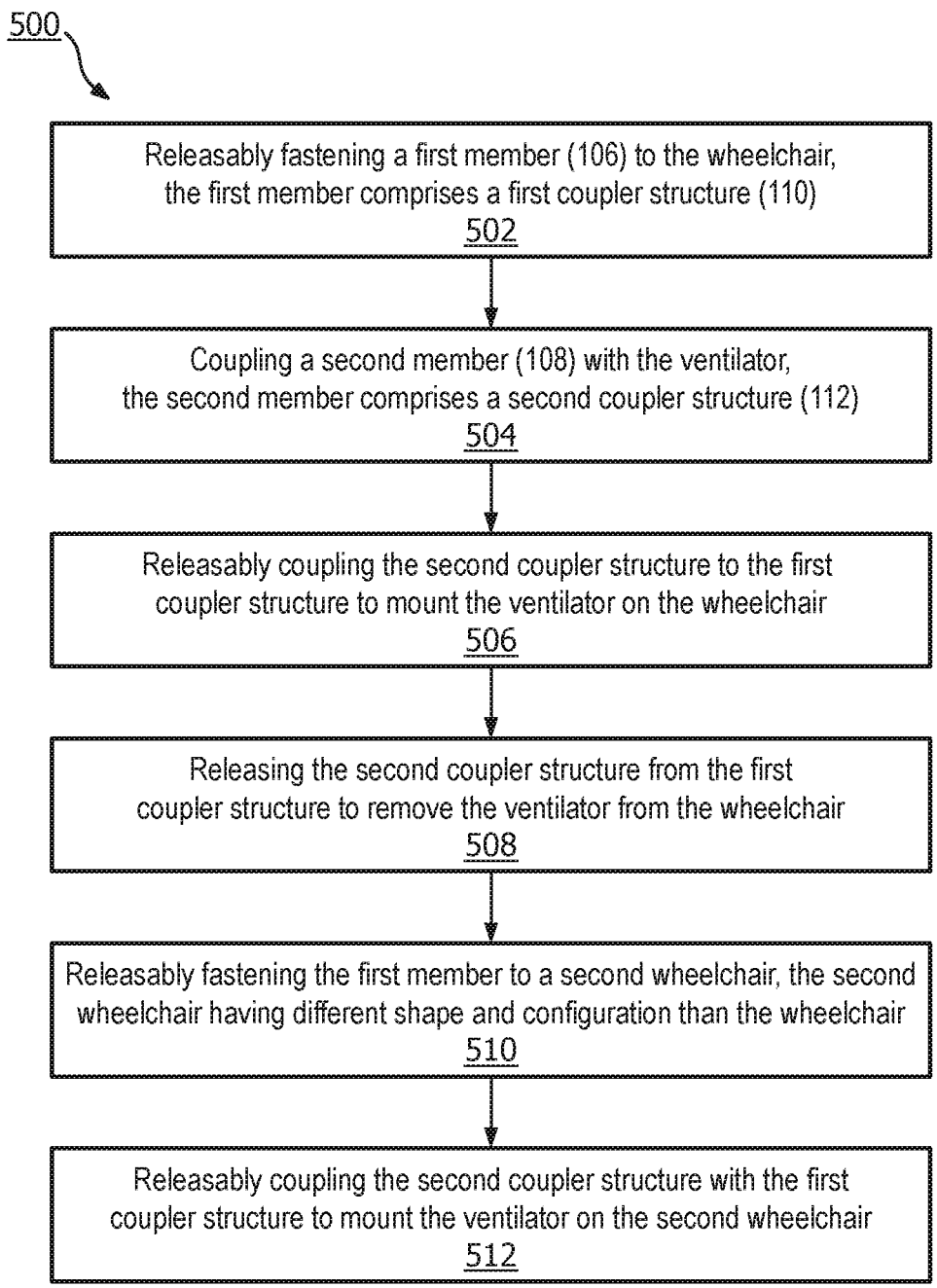
FIG. 17 shows an exemplary method for mounting a ventilator on a wheelchair in accordance with an embodiment of the present patent application.

FIG. 17 illustrates an exemplary method 500 for mounting ventilator 102 on wheelchair 104. The procedures of method 500 presented herein are intended to be illustrative. In one embodiment, method 500 may be accomplished with one or more additional procedures not described, and/or without one or more of the procedures discussed. Additionally, the order in which the procedures of method 500 is illustrated in FIG. 17 and described herein is not intended to be limiting.

At procedure 502 of method 500, first member 106 is releasably fastened to wheelchair 104, where first member 106 includes first coupler structure 110. At procedure 504 of method 500, second member 108 is coupled with ventilator 102, where second member 108 comprises second coupler structure 112.

At procedure 506 of method 500, second coupler structure 112 is releasably coupled with first coupler structure 110 to mount ventilator 102 on wheelchair 104. At procedure 508 of method 500, second coupler structure 112 is released from first coupler structure 110 to remove ventilator 102 from wheelchair 104. For example, when second coupler structure 112 is released from first coupler structure 110, the user can simply remove ventilator 102 from wheelchair 104.

The user can, thereafter, mount the same ventilator 102 on a second wheelchair $WC_1$, $WC_2$, $WC_3$, or $WC_4$ (as shown in FIGS. 11-16). For example, at procedure 510 of method 500, first member 106 is releasably fastened to second wheelchair $WC_1$, $WC_2$, $WC_3$, or $WC_4$ (as shown in FIGS. 11-16), wherein second wheelchair $WC_1$, $WC_2$, $WC_3$, or $WC_4$ has different shape and configuration than wheelchair 104. At procedure 512 of method 500, second coupler structure 112 is releasably coupled with first coupler structure 110 to mount ventilator 102 on second wheelchair $WC_1$, $WC_2$, $WC_3$, or $WC_4$.

The present patent application provides a universal ventilator mounting solution that enables ventilator 102 to mount on the back of just about any wheelchair. System 100 is also configured to allow for easy mounting of ventilator 102 on wheelchair 104 anytime and anywhere by the user and for easy release/detachment of ventilator 102 from wheelchair 104 anytime and anywhere by the user. System 100 is also configured to allow the user to change their wheelchair, without having to upgrade/change their mounting system.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for mounting a ventilator on a wheelchair, the system comprising:
a first member configured to be releasably fastened to the wheelchair, the first member comprising a first coupler structure; and
a second member coupled with the ventilator, the second member comprising a second coupler structure that is configured to be releasably coupled with the first coupler structure to mount the ventilator on the wheelchair;
wherein the first member comprises one or more strap members and one or more interengaging fastener elements that are configured to releasably fasten the first member to a portion of the wheelchair; and
wherein each of the first coupler structure and the second coupler structure comprises one of hook elements or loop elements that are complimentary to one another and configured to releasably mount the ventilator behind a backrest of the wheelchair.

2. The system of claim 1, wherein the one or more strap members are configured to be adjustable in their length to releasably fasten the first member to the portion of the wheelchair.

3. The system of claim 1, wherein the system is configured to mount the ventilator on a second wheelchair, the second wheelchair having different shape and configuration than the wheelchair.

4. A method for mounting a ventilator on a wheelchair, the method comprising:
releasably fastening a first member to the wheelchair, the first member comprising a first coupler structure;
coupling a second member with the ventilator, the second member comprising a second coupler structure; and
releasably coupling the second coupler structure with the first coupler structure to mount the ventilator on the wheelchair;
wherein the first member comprises one or more strap members and one or more interengaging fastener elements that are configured to releasably fasten the first member to a portion of the wheelchair; and
wherein each of the first coupler structure and the second coupler structure comprises one of hook elements or loop elements that are complimentary to one another and configured to releasably mount the ventilator behind a backrest of the wheelchair.

5. The method of claim 4, wherein the one or more strap members are configured to be adjustable in their length to releasably fasten the first member to the portion of the wheelchair.

6. The method of claim 4, further comprising:
releasing the second coupler structure from the first coupler structure to remove the ventilator from the wheelchair;
releasably fastening the first member to a second wheelchair, the second wheelchair having different shape and configuration than the wheelchair; and
releasably coupling the second coupler structure with the first coupler structure to mount the ventilator on the second wheelchair.

7. A system for mounting a ventilator on a wheelchair, the system comprising
means for releasably fastening to the wheelchair, the means for releasably fastening comprising a first means for releasably coupling; and
means for coupling with the ventilator, the means for coupling comprising a second means for releasably coupling that is configured to be releasably coupled with the first means for releasably coupling to mount the ventilator on the wheelchair;
wherein the means for releasably fastening comprises one or more strap members and one or more interengaging fastener elements that are configured to releasably fasten the means for releasably fastening to a portion of the wheelchair; and
wherein each of the first and second means for releasably coupling comprises one of hook elements or loop elements that are complimentary to one another and configured to releasably mount the ventilator behind a backrest of the wheelchair.

8. The system of claim 7, wherein the one or more strap members are configured to be adjustable in their length to releasably fasten the first member to the portion of the wheelchair.

9. The system of claim 7, wherein each of the first means for releasably coupling and the second means for releasably coupling comprises one or more coupler elements, and wherein the one or more coupler elements of the first means for releasably coupling are configured to releasably couple with the one or more coupler elements of the second means for releasably coupling to mount the ventilator on the wheelchair.

10. The system of claim 7, wherein the system is configured to mount the ventilator on a second wheelchair, the second wheelchair having different shape and configuration than the wheelchair.

* * * * *